US00PP20234P3

(12) United States Plant Patent
Nettleton et al.

(10) Patent No.: US PP20,234 P3
(45) Date of Patent: Aug. 25, 2009

(54) BLACK BERRY PLANT 'NETTLETON CREAMY WHITE'

(50) Latin Name: *Rubus Fruticosus*
Varietal Denomination: Nettleton Creamy White

(75) Inventors: Scott E. Nettleton, Olney, IL (US); John R Nettleton, 1125 Country Club La., Corona, CA (US) 92880

(73) Assignee: John R Nettleton, Corona, CA (US)

( * ) Notice: Subject to any disclaimer, the term of this patent is extended or adjusted under 35 U.S.C. 154(b) by 0 days.

(21) Appl. No.: 11/510,731

(22) Filed: Aug. 28, 2006

(65) Prior Publication Data

US 2008/0196130 P1 Aug. 14, 2008

(51) Int. Cl.
*A01H 5/00* (2006.01)

(52) U.S. Cl. ..... Plt./203

(58) Field of Classification Search ..... Plt./203
See application file for complete search history.

(56) References Cited

U.S. PATENT DOCUMENTS

PP14,935 P2 * 6/2004 Clark ..... Plt./203

* cited by examiner

*Primary Examiner*—Susan B McCormick Ewoldt

(57) ABSTRACT

A new and distinct variety of upright blackberry plant that in all characteristics looks similar to a wild blackberry but is distinct in that the fruit when fully ripened is the color of an almost translucent creamy white and not the reddish purple color of the wild blackberry. The new variety named "Nettleton Creamy White" is an upright plant, is a biennial, thorny, with five leaves per stem along the canes. The berries are produced on the $2^{nd}$ year canes and are larger then the standard wild blackberry fruit. The creamy white fruit is medium in size and has a sweet taste to them. The cane and leaves are light to bright green and have the absence of the anthocyanin coloration.

11 Drawing Sheets

Figure 1:
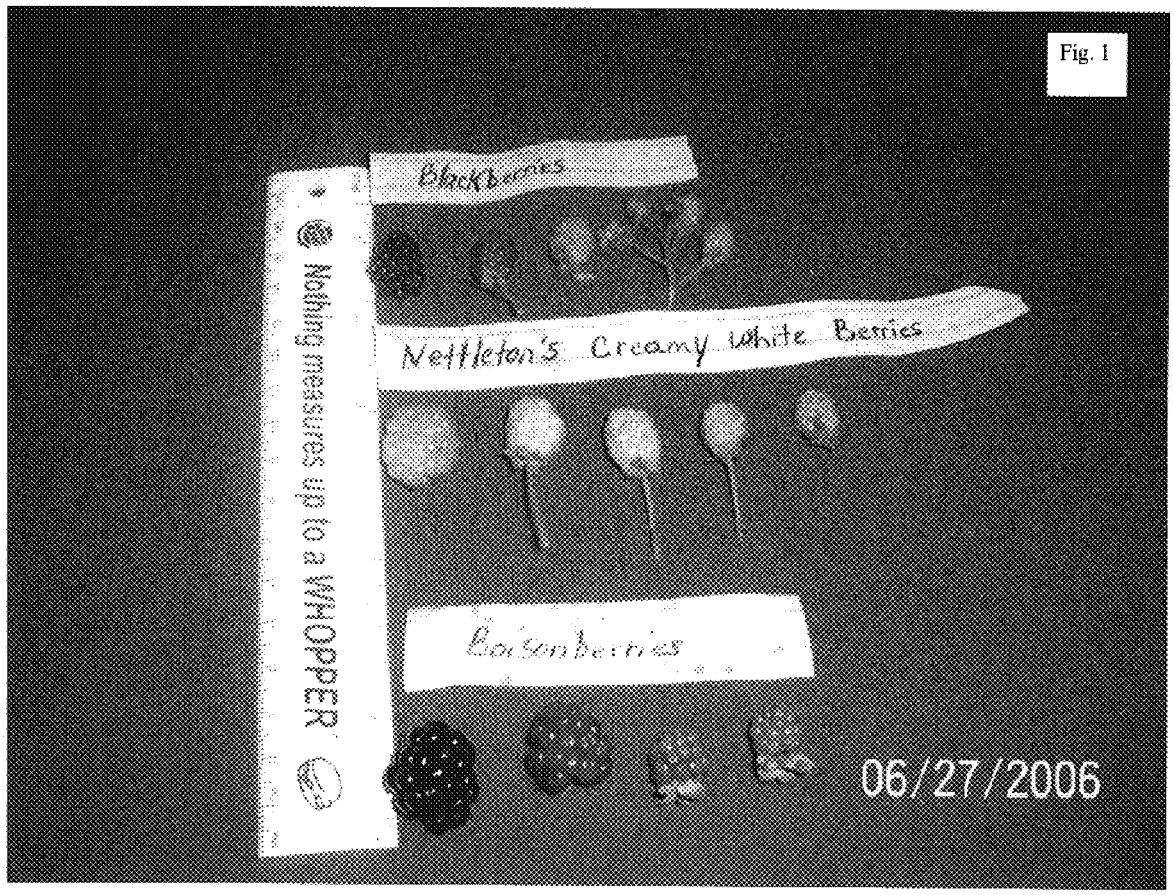

*Rubus fruticosus*: Variety 'Nettleton Creamy White'.

BACKGROUND OF THE INVENTION

This new variety of Blackberry plant named the 'Nettleton Creamy White' is the result of a whole plant spontaneous mutation of the common wild blackberry, *Rubus Fruticosus* found in Southern Illinois. The plant was found on cultivated land in South Central Illinois (Richland County). The plants of this new variety of erect blackberry plant lack the anthocyanin pigmentation in the plant canes and leaves and the fruit is of a creamy white color when mature, which is unlike the normal purple coloring found in wild or domestic blackberries. This new variety of blackberry is similar to other upright varieties of blackberry cultivars, with the biennial canes with the $1^{st}$ year canes going dormant during the wintertime and then in the spring, as second year canes will flower and produce fruit. After the fruit production season, the $2^{nd}$ year canes die off. The new variety of upright blackberry has some similarities to the 'Clark Gold', U.S. Plant Pat. No. 14,935, a trailing vine dewberry plant with yellow fruit and the 'Kiwigold', U.S. Plant Pat. No. 11,313, a red raspberry mutation also with yellow fruit. This new variety of blackberry differs from the 'Clark Gold' in that it is an upright cane plant; verses the 'Clark Gold' that is a trailing vine cane plant. In addition, the 'Clark Gold' as a dewberry flowers and produces fruit in April–May where the new variety flowers and produces fruit in June–July.

This new variety of blackberry plant is also distinguished by its cane and leaf coloring. As a new small plant the plant has, a light-green coloring as it grows and matures the green darkens to a bright green, as do the leaves. The $2^{nd}$ year canes change color from the bright green to a woody brown color. The standard blackberry, dewberry and boysenberry plants have a red and green coloring running through out the canes and leaves, which is the presence of anthocyanin. The 'Nettleton Creamy White' Blackberry does not have this red coloring in it. The flowers are a white color. The berries are a light green and as they mature to a ripened state, they become a creamy white color.

The purposed "Nettleton Creamy White" blackberry is to be grown for the purpose of being propagated and sold through various types of outlets to the general public, plant nurseries and possibly food processing companies as well. The fruit is good for eating fresh. To be used in making pies, jams, jellies, preserves or can be made into a juice and can be frozen for later use.

SUMMARY OF THE INVENTION

The original plant was discovered in an old garden, among some wild blackberries, on a farm, near Noble, Richland County, South Central Illinois in 1999. The plant was transplanted to another garden plot, about 10 to 15 miles away, where it has been growing and asexually reproducing for the past 9 years. The plant asexually reproduces from sprouts coming up from the roots at the base of the plant. When the sprouts are matured enough they can be dug up and separated from the mother plant. Each plant has the same characteristics as the mother plant from which it was produced. Producing the same type of plant, canes, leaves and the same type of 'Creamy White' fruit.

This new variety of blackberry from Illinois has also been growing in a garden in southern California for over a year.

BRIEF DESCRIPTION OF ILLUSTRATIONS

Figure 2:
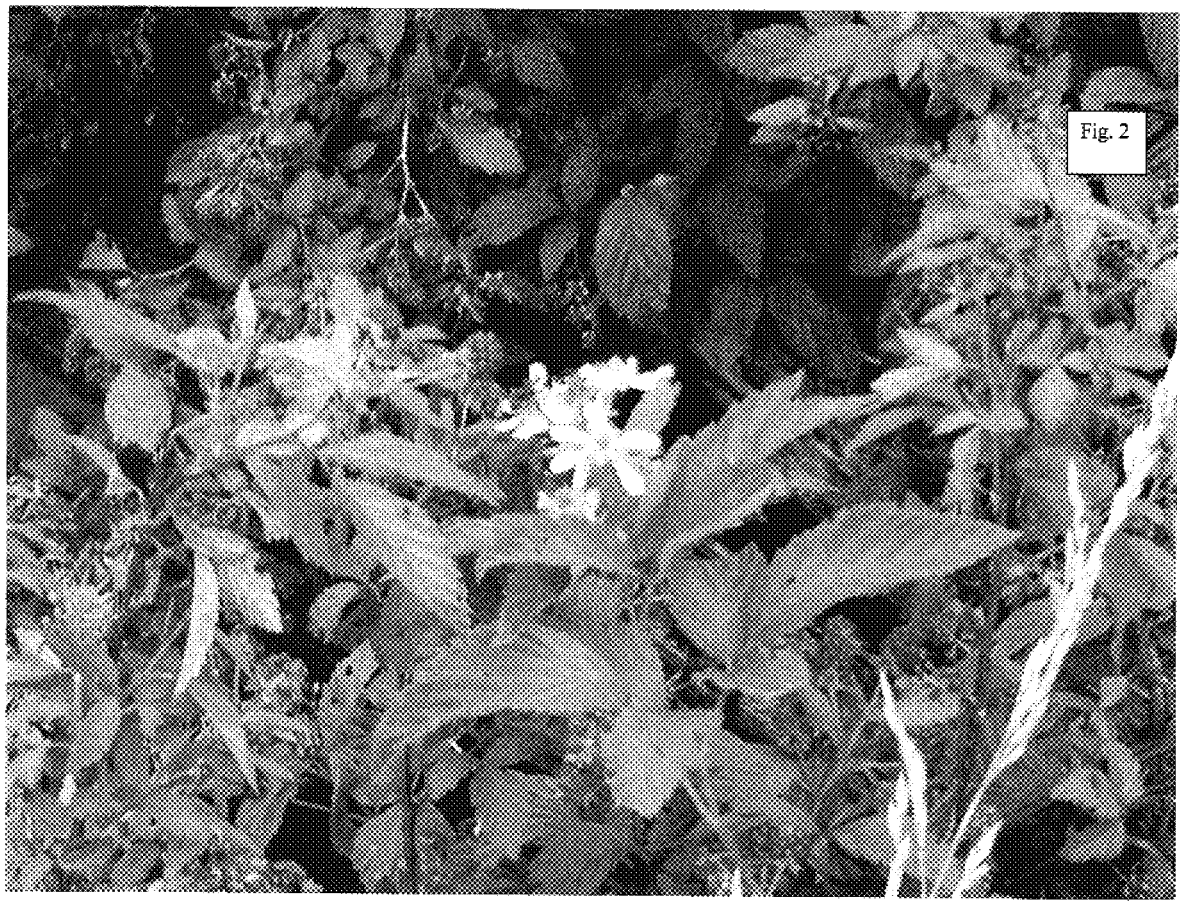
Figure 3:
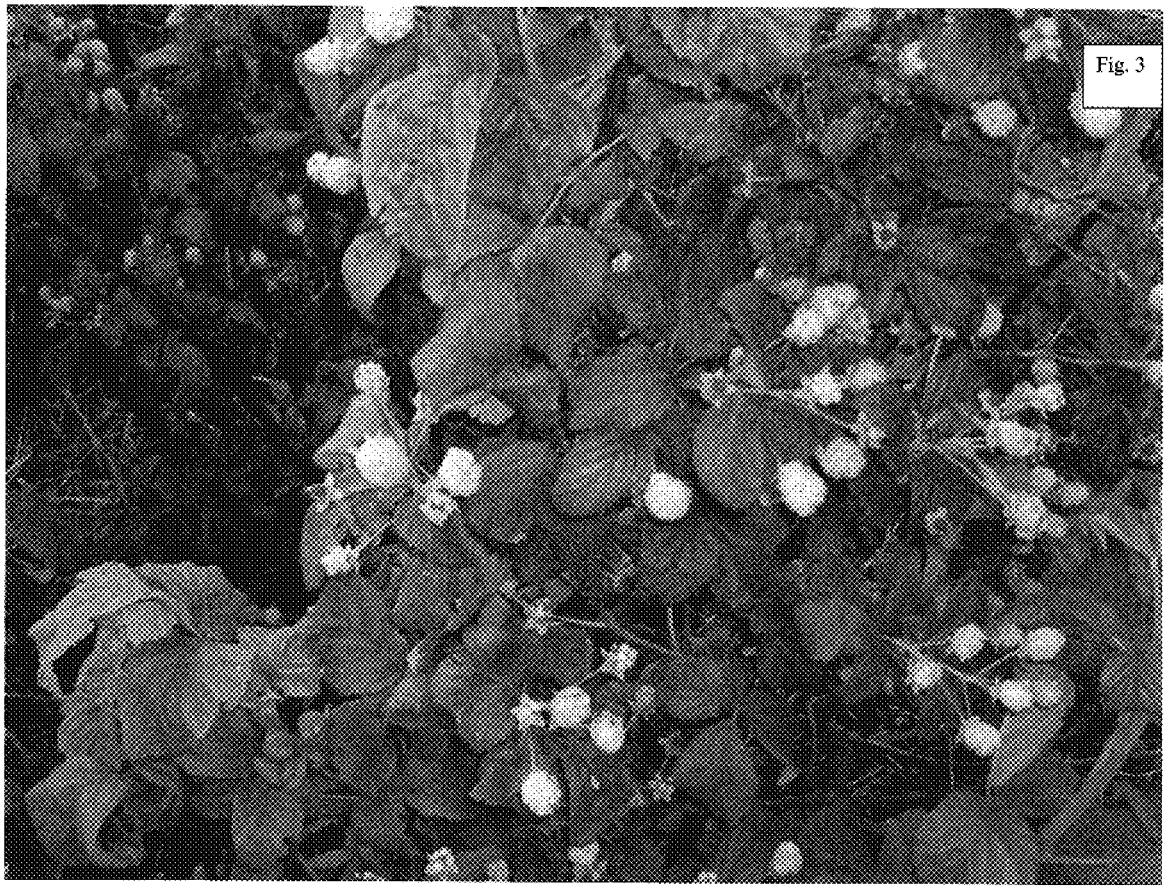
Figure 4:
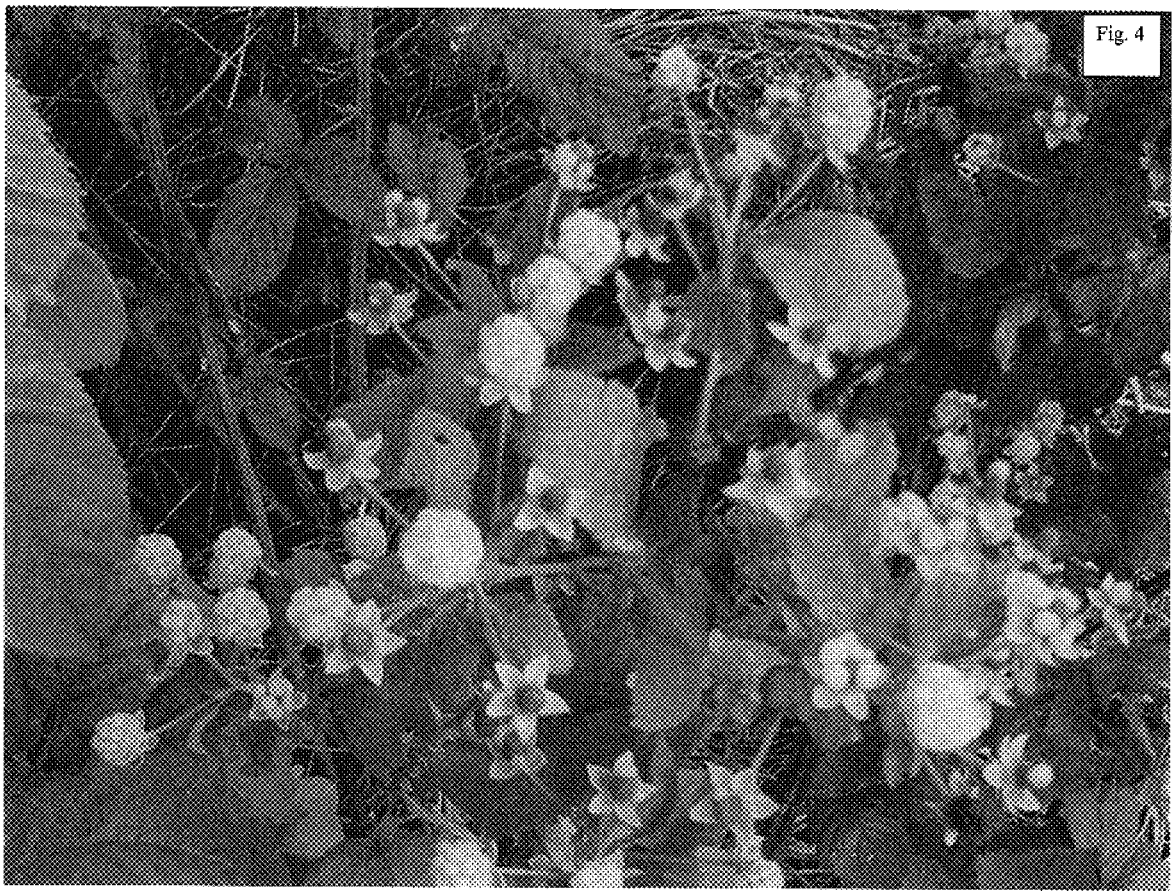
Figure 5:
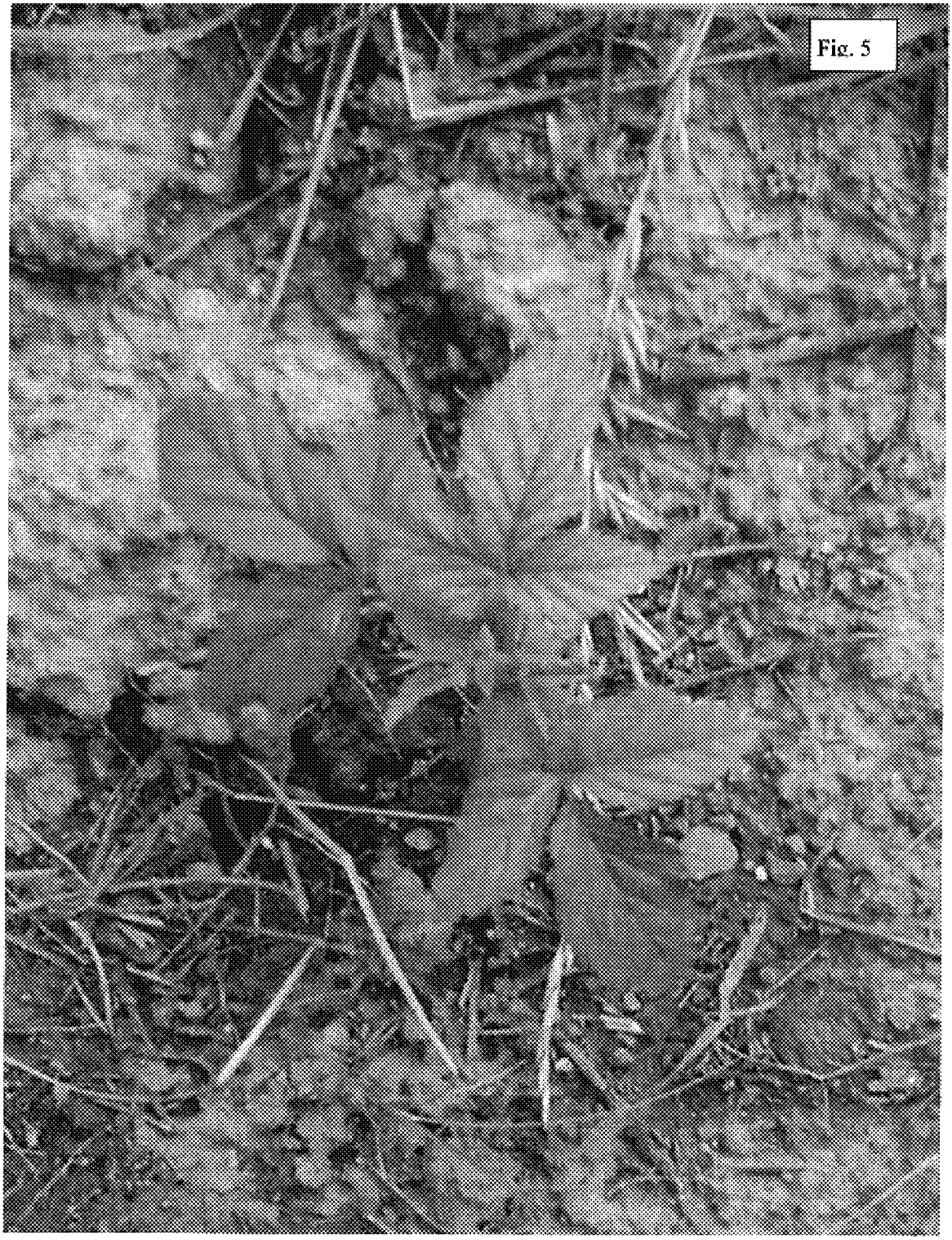
Figure 6:
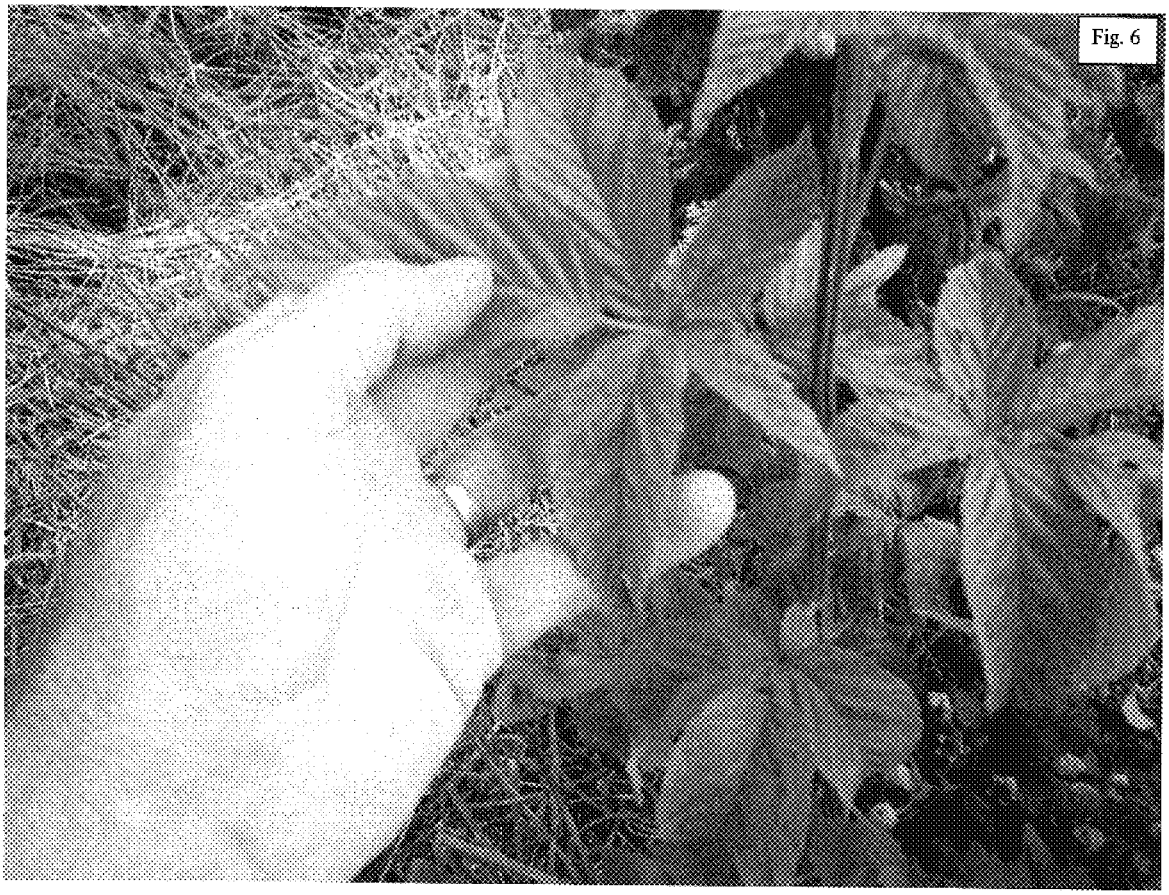
Figure 7:
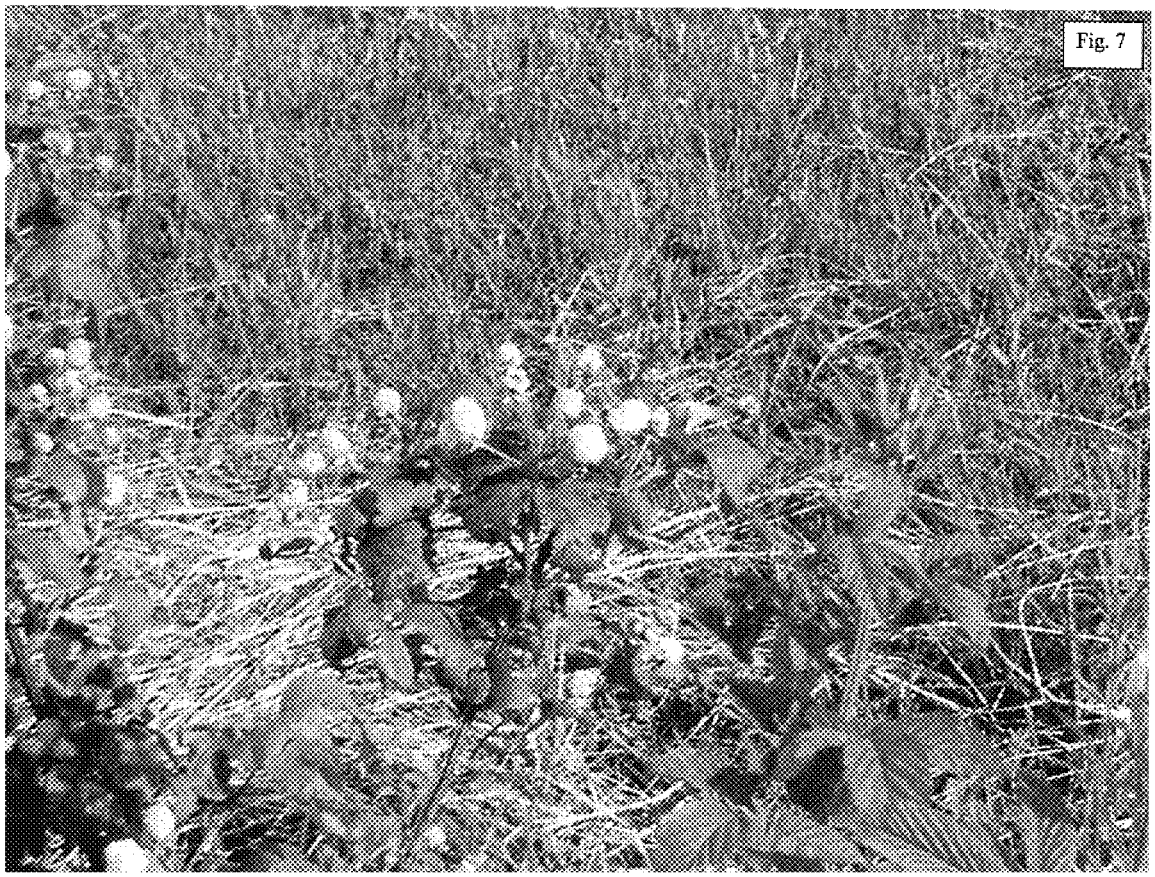
Figure 8:
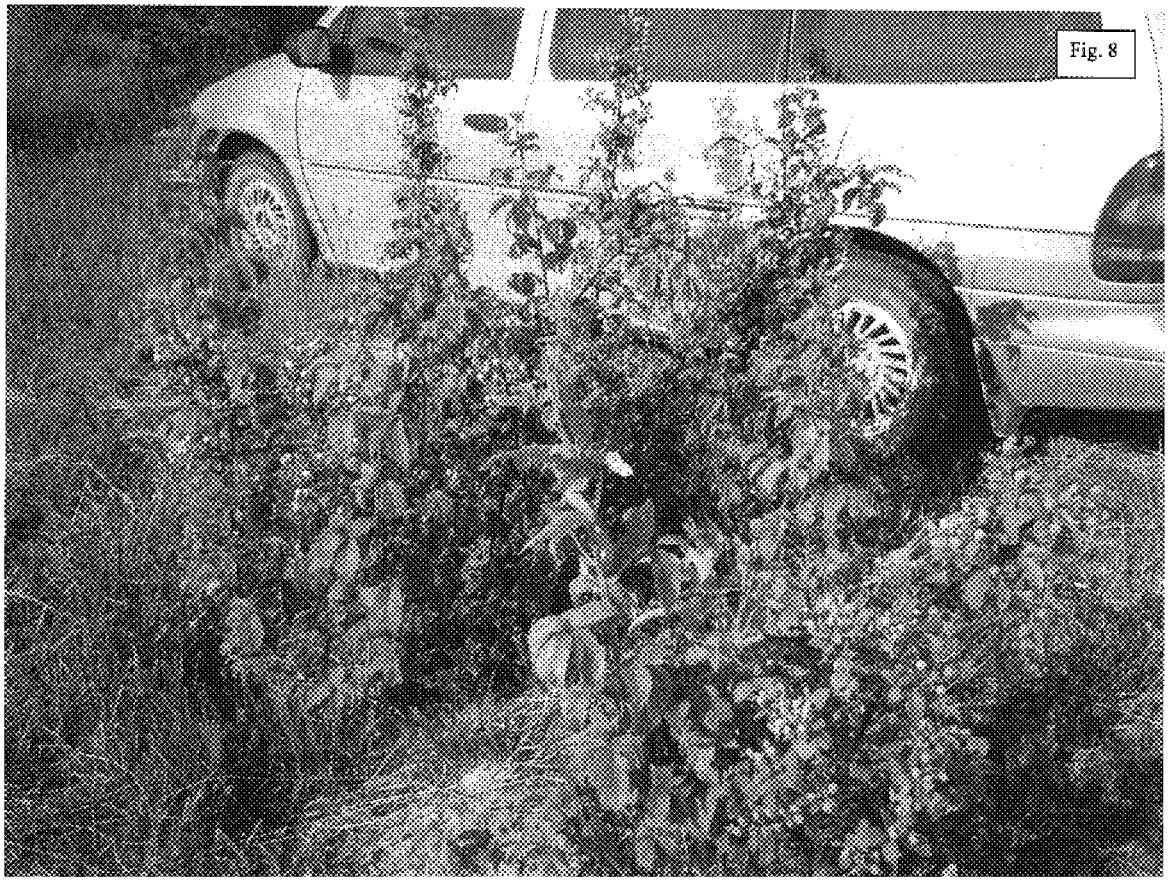
Figure 9:
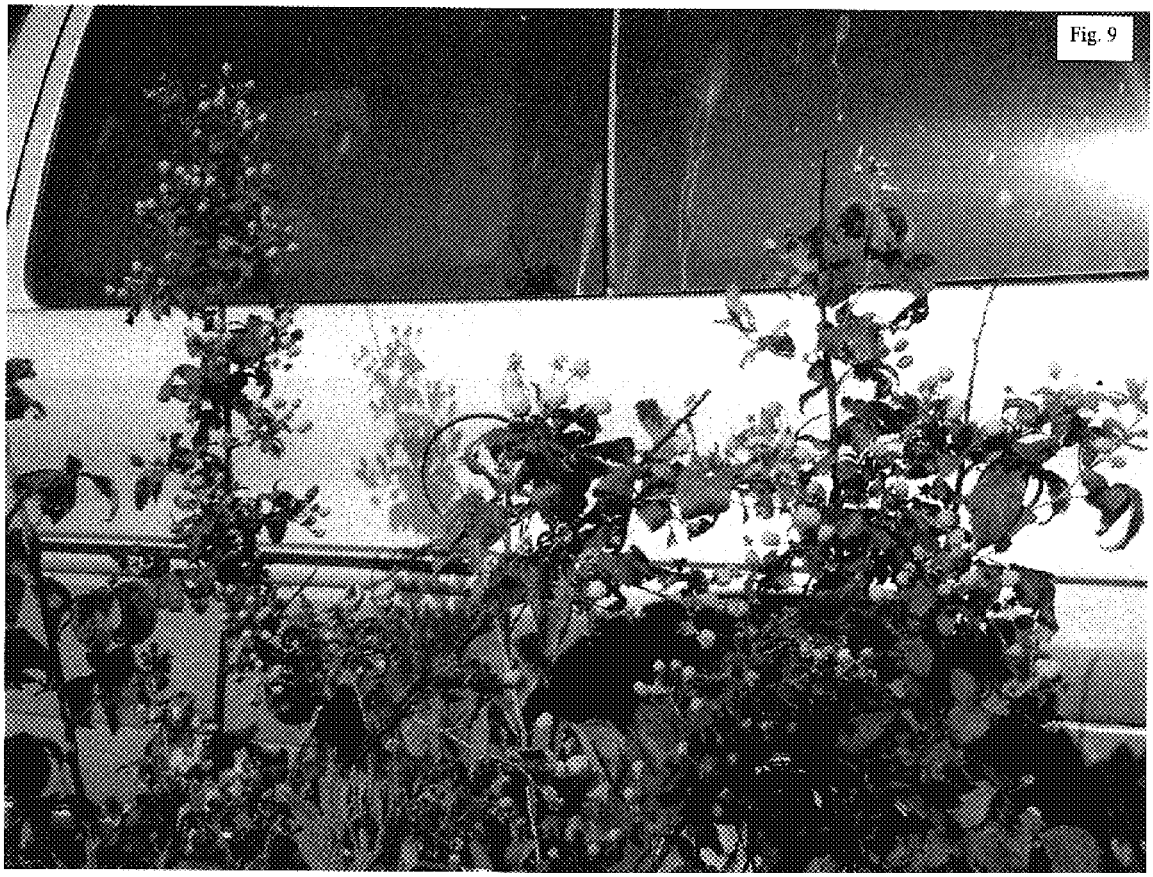
Figure 10:
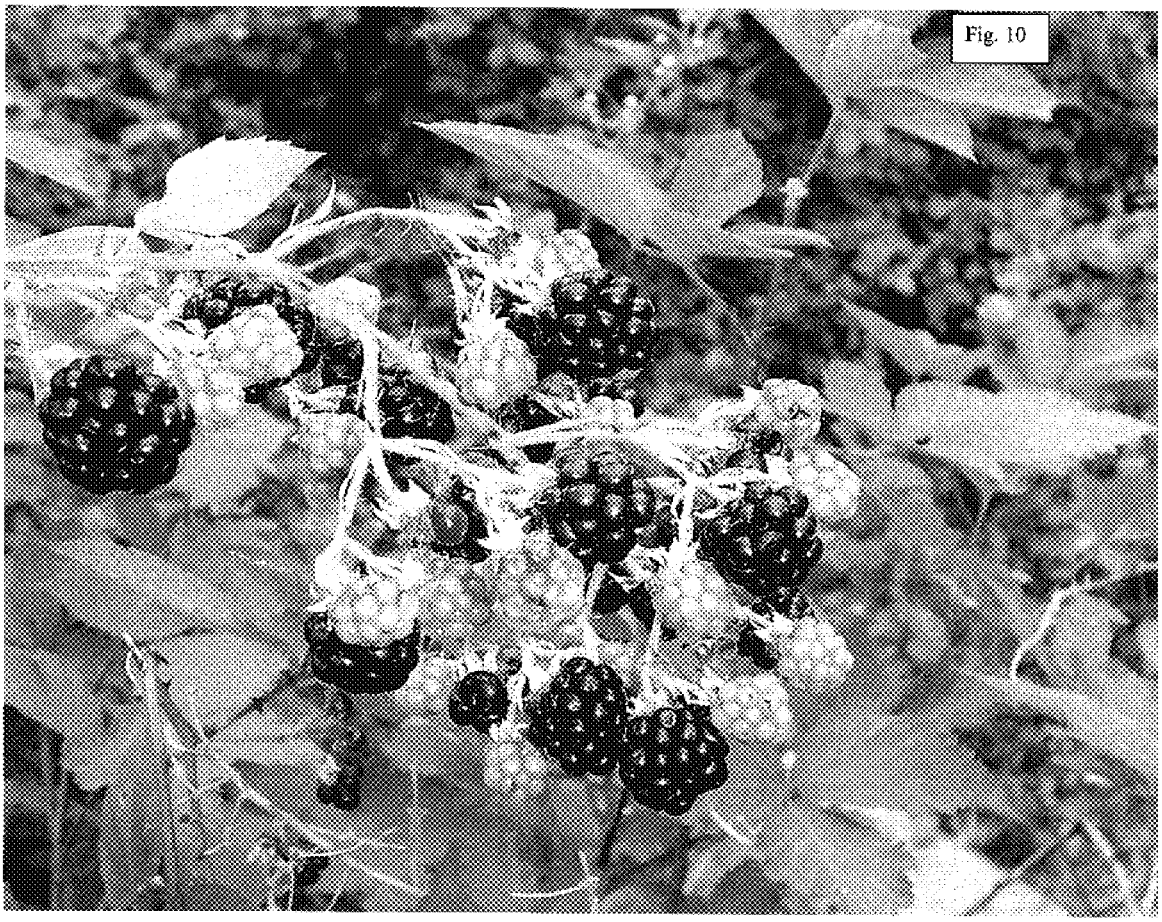
Figure 11:
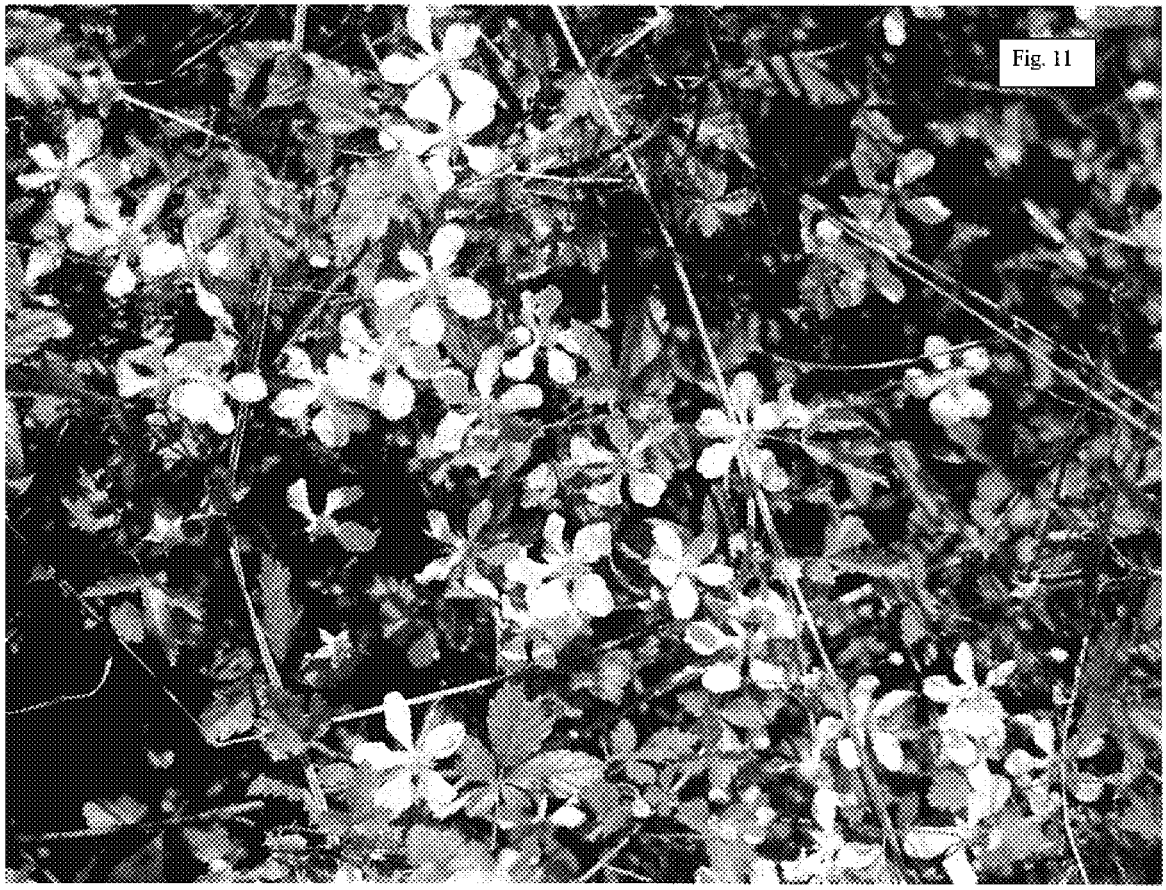

FIG. 1 Comparison of the fruit of "wild blackberries", 'Nettleton Creamy White' berries and "boysenberries" in the various stages of ripening FIG. 2 Southern Illinois wild blackberries growing on the property of Scott Nettleton FIG. 3 "Nettleton Creamy White" blackberries in various stages of ripening. Also showing the size and shape of the sepals can be seen FIG. 4 Close up of "Nettleton Creamy White" blackberry plants showing the Sepals, the Cores, the berries in early and middle stages of ripening FIG. 5 New plant "Nettleton Creamy White" blackberry FIG. 6 Close-up of mature plant "Nettleton Creamy White" showing leaves and cane FIG. 7 "Nettleton Creamy White" plants showing 2$^{nd}$ year canes with fruit and 1$^{st}$ canes from new growth FIG. 8 Small patch of "Nettleton Creamy White" blackberries, 2$^{nd}$ year canes with fruit on them and new 1$^{st}$ year canes FIG. 9 Showing the quantity of berries produced per each cane. "Nettleton Creamy White" berries FIG. 10 Wild blackberries—showing quantities of berries produced per each cane and the red to black stages ripening stages of the berries FIG. 11 Dewberry vines and flowers—showing quantities of berries produced per each cane

BOTANICAL DESCRIPTION OF THE PLANT

The descriptions given in this section are from plants grown in Richland County, Ill. The color data used in this report was taken from Royal Horticultural Society (R.H.S.) Colour charts. When dimensions, sizes, colors and other characteristics are given, they are given as averages and not as specifics. The data given is accurate as can be at this time.

Plant:

*Size.*—Average height of the upright canes are from five to six feet depending on soil conditions.

Canes: Medium size and upright with thorns up and down the canes and along the leaf stems. (Primocanes) average diameter is ⅜" to ⅝". Color Yellow Green Group (146C). Thorn length — an average of about ¼". (Floricanes) average diameter is ⅝". Thorn length — an average of about ¼". Floricane and Thorn Color — Yellow-Green Group (146B).

Foliage:

*Primocane.*—Leaves — primary leaves are 3" in length; 3 to 5 leaves per stem; Shape — broad elliptic with acute apex with cerated edges. Color of abaxial and adaxial surfaces Yellow Green Group (137A). Leaf midvein color; Green Group (137A).

Floricane:

*Leaves.*—Primary leaves are 3" in length, secondary leaves are 2" in length; width — 1½" to 2". Shape — broad elliptic with acute apex with cerated edges. Color of abaxial and adaxial surfaces Yellow Green Group (137A). Leaf midvein color; Green Group (137A); 3 leaves per stem.

Flowers: Mostly solitary on erect branch peduncles, with Seven flowers per branch. Date of Bloom — First — Average around Julian 150: 50% around Julian 164: Last around Julian 180. Blossom Color — White: Petal Color — White Group (155D). Reproductive Organs. — Stamens — erect several. Pistils — several. Pollen — normal. Stamen color — Yellow-Green Group (153A); stigma color — Yellow Green Group (151D).

Flower diameter: Average of 2½". Petal size — length — average of 1". Width — average of ½". Number of petals per flower. — 5. Calyx. — Sepals are elongated, oval shape with smooth edges. Peduncle length. — 2¼". Peduncle color, — Yellow Green Group (146B).

Fruit: Maturity. — Average first day is around July 3$^{rd}$. Average ripening time is from July 3$^{rd}$ until July 17$^{th}$. Size. — Averages about ⅝" to ¾" in diameter, which is a little larger then the wild blackberries. Length — Averages about ¾". Shape — predominately oval to circular. Color: Light Creamy White color almost translucent. Seed. — small, about 2.0 mg/seed. Color — Creamy White RHS 155D.

Disease: Plants the plants seem to be disease resistant as pertaining to plant diseases found in Southern Illinois. Not aware of diseases in other states that would affect this new variety of Blackberry.

Storage of fruit: Ripened fruit can be frozen in bags or containers and stored up to 6 to 8 months.

Shipping of fruit: Information not available at this time.

Asexual reproduction — the plants were asexually reproduced by producing new plants from the roots at the base of the canes in a cultivated garden in Olney, Ill. The berries also have a very sweet taste. The drupelets are like the blackberry and are attached to the center core. When the berries are fully ripe they can be removed from the plant by shaking the canes and the berries will fall off. The variety — The most distinctive characteristics of this new variety of upright blackberry is the creamy white color of the fruit and the light green to dark green coloring of the canes and leaves, which have the absence of the anthocyanin pigmentation. Both primocanes and floricanes are thorny, erect cane plant types The new variety originated in USDA hardiness zones 6.

We claim:

1. A new and distinctive variety of upright blackberry plant, substantially as described and illustrated herein, and is characterized by having a creamy white colored fruit with the absence of anthocyanin coloration in the canes and of leaves of the plant.

* * * * *